United States Patent
Florence et al.

(10) Patent No.: US 6,194,543 B1
(45) Date of Patent: Feb. 27, 2001

(54) DENDRITIC POLYPEPTIDES

(75) Inventors: Alexander T. Florence; Thiagarajan Sakthivel; Andrew F. Wilderspin; Istvan Toth, all of London (GB)

(73) Assignee: The school of Pharmacy University (GB)

( * ) Notice: Subject to any disclaimer, the term of this patent is extended or adjusted under 35 U.S.C. 154(b) by 0 days.

(21) Appl. No.: 09/096,411

(22) Filed: Jun. 11, 1998

(30) Foreign Application Priority Data

Jun. 11, 1997 (EP) .................................. 97304060

(51) Int. Cl.[7] .................................. A61K 38/04
(52) U.S. Cl. .................. 530/300; 530/327; 530/328; 530/329; 530/330; 530/332; 514/2; 514/15; 514/16; 514/17
(58) Field of Search .................. 530/327, 328, 530/329, 330, 300, 332, 345; 514/2, 15, 16, 17

(56) References Cited

U.S. PATENT DOCUMENTS

| | | | |
|---|---|---|---|
| 4,289,872 | * 9/1981 | Denkewalter | 528/328 |
| 5,114,713 | 5/1992 | Sinigaglia | 424/88 |
| 5,338,532 | * 8/1994 | Tomalia | 424/1.9 |
| 5,488,126 | * 1/1996 | Subramanian | 558/17 |
| 5,580,563 | * 12/1996 | Tam | 424/197.11 |
| 5,795,582 | * 8/1998 | Wright | 424/400 |

FOREIGN PATENT DOCUMENTS

| | | |
|---|---|---|
| WO89/10348 | 11/1989 | (WO) . |
| WO93/22343 | 11/1993 | (WO) . |
| WO94/02506 | 2/1994 | (WO) . |
| WO94/11015 | 5/1994 | (WO) . |
| WO95/00540 | 1/1995 | (WO) . |

OTHER PUBLICATIONS

CRS Symposium, Las Vegas, Jun. 21–25, 1998; A Dendrimer Carrier; Preliminary Investigations on Biodistribution and Stability; T. Sakthivel, A.T. Florence and I. Toth.

EUFEPS Conference, Milan, Italy, Sep. 11–13, 1998; Oral Absorption of a Novel Dendrimer Carrier; T. Sakthivel, A.T. Florence and I. Toth.

2nd European Workshop on Particulate Systems Paris, May 22–23, 1998 An Investigation into Novel Lipidic Dendrimer Carrier; T. Sakthivel, I. Toth and A.T. Florence.

"A Novel Chemical Approach to Drug Delivery: Lipidic Amino Acid Conjugates"; Istvan Toth; Journal of Drug Targeting; 1994; vol. 2, pp. 217–239.

"Immunogenicity Evaluation of a Lipidic Amino Acid–Based Synthetic Peptide Vaccine for Chalamydia Tracomatis"; Guangming Zhong, et al.; The Journal of Immunology; vol. 151, 3728–3736; No., 7; Oct. 1, 1993.

"Macromolecular Assemblage in the Design of a Synthetic AIDS Vaccine"; Jean–Philippe DeFoort, et al.; Proc. Natl. Acad, Sci. USA; vol. 89; pp. 3879–3883; May 1992 (Biochemistry).

"Synethic Peptide Vaccine Design: Synthesis and Properties of a High–Density Multiple Antigenic Peptide System": James P. Tam; Proc. Natl. Acad. Sci. USA; vol. 85 pp. 5409–5413; Aug. 1998 (Biochemistry).

* cited by examiner

Primary Examiner—Christopher S. F. Low
Assistant Examiner—David Lukton
(74) Attorney, Agent, or Firm—Ostrolenk, Faber, Gerb & Soffen, LLP

(57) ABSTRACT

A dendritic compound comprises two dendrons, each comprising dendritically linked amino acid units, preferably lysine units, joined to a focal group. One of the dendrons includes terminal branches including anchor groups constituted by hydrophobic units and the second dendron has terminal branches which are linked or may be linked to active ligands or sugar moieties. Methods for synthesising the dendritic compounds using solid phase peptide synthetic techniques including lipidic amino acid reagents is described. The compounds serve as a basis for multiple antigenic peptides or drug delivery systems.

25 Claims, 4 Drawing Sheets

DENDRITIC POLYPEPTIDES

BACKGROUND OF THE INVENTION

Tam et al. in *Proc. Natl. Acad. Sci. USA*(1985) 85, 5409 5413 describe a compound including a dendritically linked polylysine component, to the focal lysine of which is attached a lipophilic moiety, through a peptide bond to the carboxylic acid group of that lysine unit. To the terminal branches of the dendritic moiety there may be attached peptide antigens to provide an active ingredient for a vaccine having improved antigenicity.

In WO-A-94/02506, Toth et al describes an improvement of Tam's invention, in which the anchor component is formed from lipophilic amino acids. This allows the compound to be synthesized using conventional solid state peptide synthetic techniques, in the first stages of which the lipophilic amino acids are linked to form, for instance, a three unit linear oligo peptide, a focal lysine unit is joined to the final lipophilic amino acid and the dendritic core moiety is then linked to the two amine groups of the focal lysine unit. The peptide antigens may subsequently be synthesized directly onto the terminal branches of the dendritic core, all the steps being carried out without cleavage of the polypeptide from the solid substrate carrier. The synthetic process used to make Toth et al's product required the use of starting amino acid reagents with the same protecting group blocking the two amine groups of lysine reagents. Consequently during the steps in which the dendritic component is synthesized, the same reagent is added to each of the amine moieties.

In the product of Toth et al, it was essential for the lipidic amino acids to be joined directly to one another by peptide bonds, and that a lipidic amino acid can be joined to a carrier substrate so that synthesis involves linkage of that until LO the carrier by a peptide bond and linkage of another lipid amino acid unit to the dendritic moiety by a peptide bond. Consequently solid state peptide synthesis methods can be used to conjugate each of the components of the final product to one another. By contrast, in Tam et al, whilst the dendritic polylysine and the peptide antigen can be synthesized using solid state peptide synthetic methods, the polylysine-polyantigen compound must be cleaved from the carrier substrate prior to conjugation to the lipophilic anchor moiety, through the carboxylic acid unit of the focal lysine group. The reagent, from which Tam's lipophilic anchor is synthesized, has only one reactive group.

BRIEF SUMMARY OF THE INVENTION

The present invention relates to polypeptide compounds which have dendritically linked units formed from amino acids having reactive groups, for instance carboxylic acid or amine groups, in their side chains. Each molecule comprises two dendrons. To at least two of the terminal branches of one of the dandrons there are attached anchor groups, each of which comprises at least one lipophilic group. The terminal units of the at least one other dendron may be unconjugated or may be conjugated to ligons of various types. The dendrons are attached at a core which may include a linear oligo peptide, optionally having pendant sugar molecules.

DETAILED DESCRIPTION OF THE INVENTION

Figure 1:
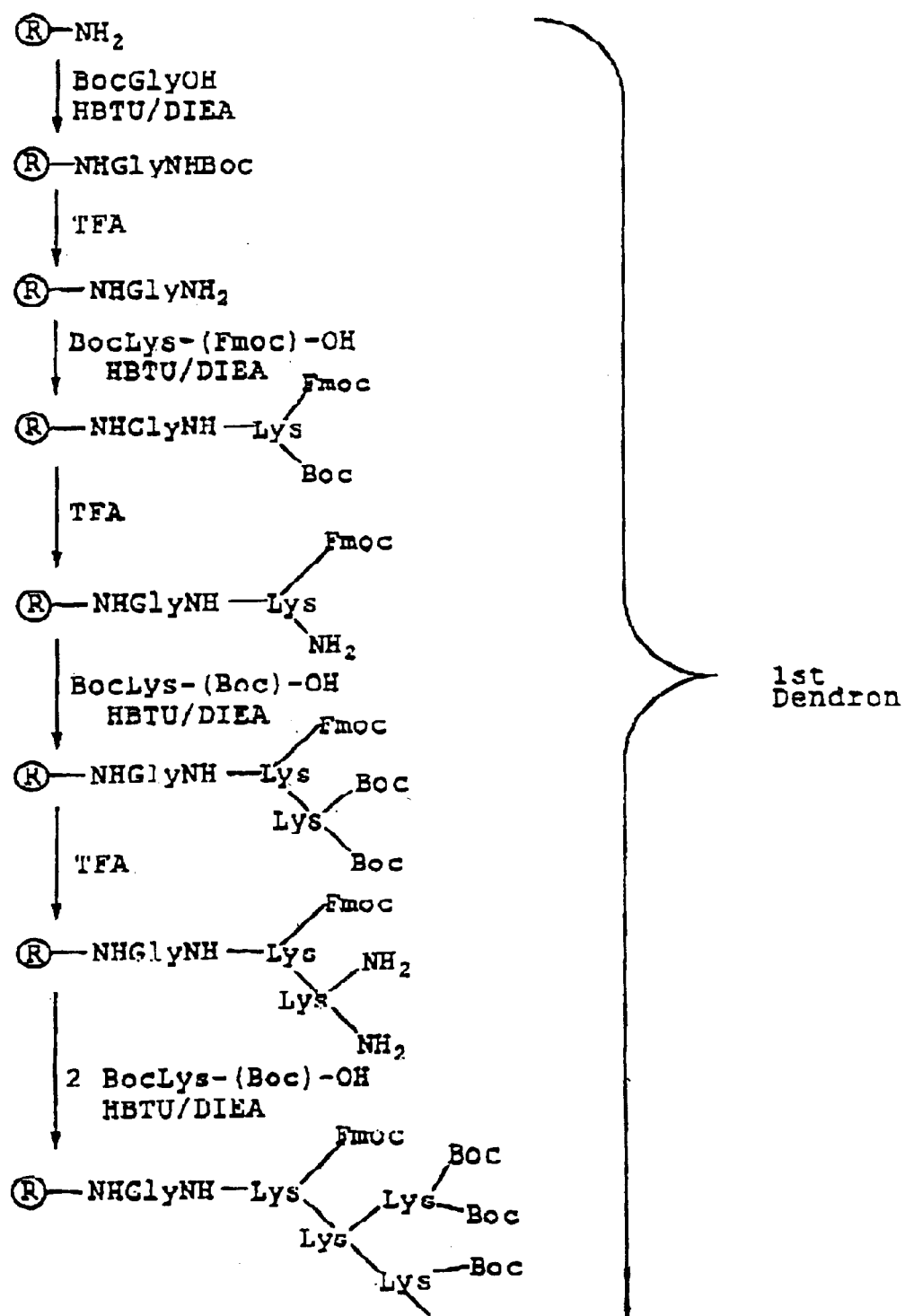
FIG. 1 is a flow diagram showing the process.
Figure 1:
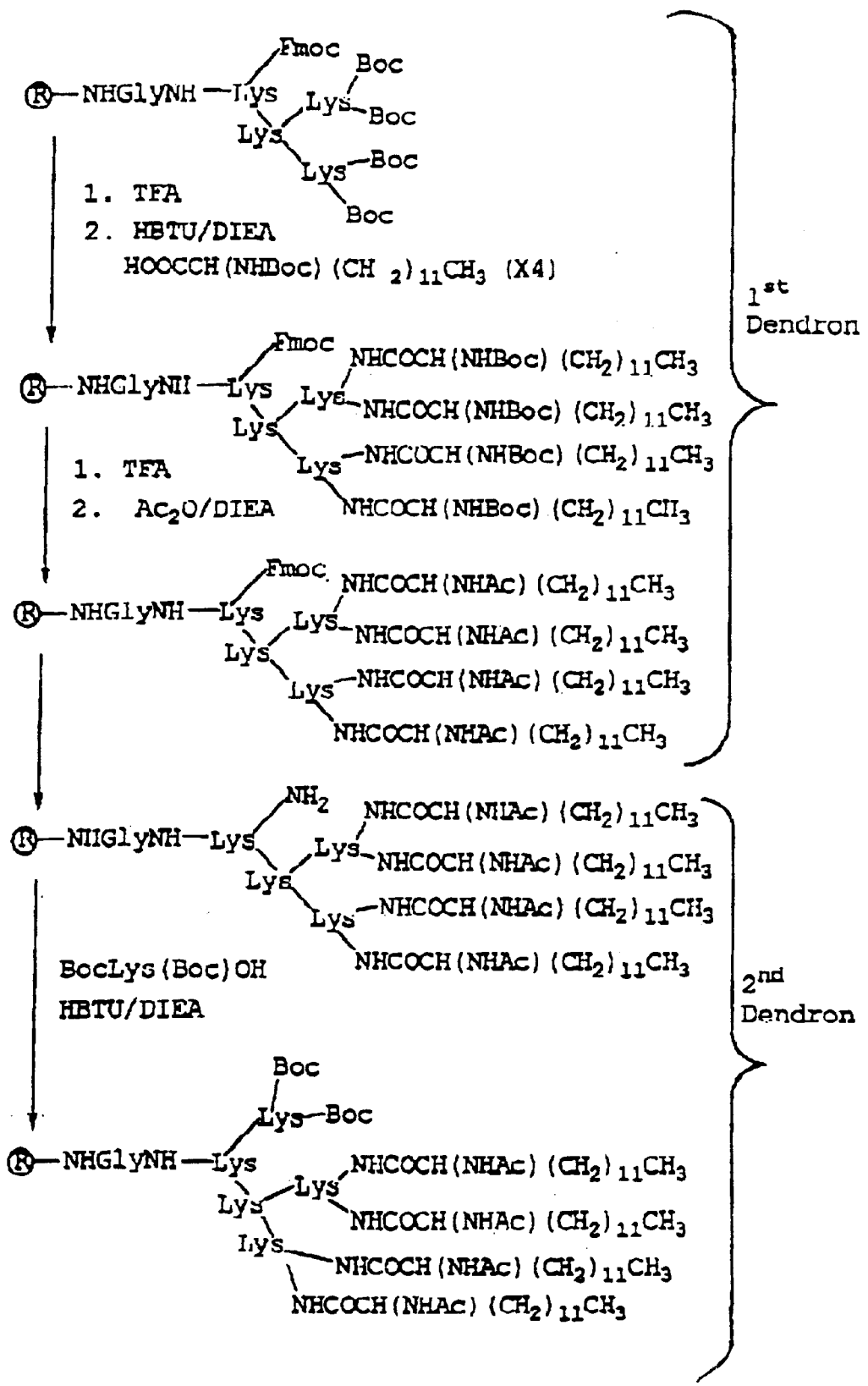
Figure 1:
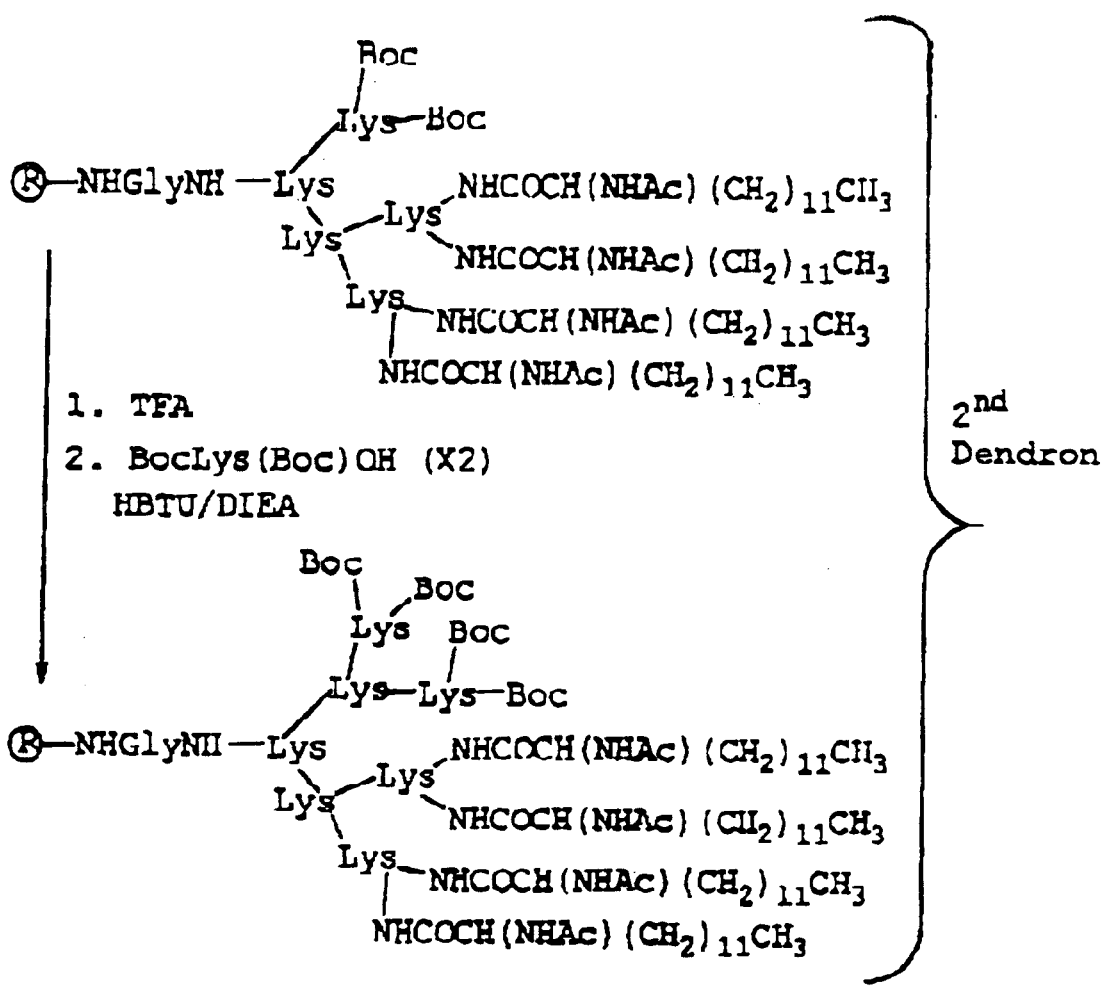

A new dendritic compound according to the present invention comprises a core including a focal group from which at least two dendrons extend, each dendron comprising dendritically linked amino acid units I

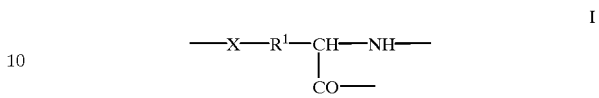

in which $R^1$ is $C_{1-6}$-alkylene and X is selected from the group consisting of —O—, —S, NH— and —CO—, and each unit of a dendron may have the same or different groups $R^1$ and X, and in which a first dendron has n levels of dendritically linked amino acid units (where n is 1 or more) and $2^n$ terminal branches, to p (where p is at least 2) of which terminal branches there are linked anchor groups $$—Y—\underset{R^2}{\underset{|}{CH}}—R^3$$

where Y is selected from —CO—, —NH—, —O— and —S—, provided that at least one of X and Y is —CO—,
$R^2$ is an organic group containing at least one $C_{6-14}$-alkyl, -alkenyl, or -alkynyl group,
$R^3$ is selected from the group consisting of hydrogen, amine, blocked amine, hydroxyl, $C_{1-24}$, alkoxy, thiol, COOH, and organic groups containing at least one $C_{6-24}$-alkyl, alkenyl or -alkynyl, $C_{1-6}$-alkanoyloxy or $C_{1-6}$-alkanamido group, any of which may be substituted by an active ligand or a sugar moiety,
and in which a second dendron has m levels (where m is 1 or more) of dendritically linked amino acid units of the formula I above in which the groups $R^1$ and X may be the same as or different to one another and the same as or different to those of the amino acid units in the first dendron and $2^m$ terminal branches, each of which is either unconjugated and is a group selected from $NH_2, N^1H_2R^{11}$, in which $R^{11}$ is hydrogen or $C_{1-4}$ alkyl, COOH, $COO^-$, OH and SH, or is conjugated via the terminal —X—, —NH— or —CO— group to a group $R^{12}$ where $R^{12}$ is a methylol group, an active ligand (which may be an anchor group as defined above) or an organic group comprising a sugar moiety.

In the present invention, the focal unit of the core is linked through covalent bond to the at least 2 dendrons. The core may include components other than the focal unit, for instance joined to the focal unit by one or more additional covalent bond. Preferably the focal unit is an amino acid unit, for instance having the formula I

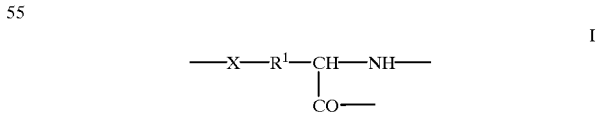

in which X and $R^1$ are as defined above.
Preferably X is either —NH— or —CO—. Where it is —CO—, the two dendrons are attached to the two —CO— moieties. Where X is NH, the two dendrons are linked one each to the groups NH. Preferably the focal unit is formed from lysine or ornithine. The third bond is joined to an organic moiety.

The core may comprise units other than the focal unit. Such units are preferably peptide linked amino acid based units. Additional core units may function merely as spacers, or may include functional groups such as lipophilic groups, hydrophilic groups or active ligands, for instance targeting groups. The compound may be attached to a resin through the focal unit, for instance via a spacer.

The present invention is made possible by the use in the synthesis of the dendritic compound of a reagent for forming the focal unit which has at least three reactive groups, each of which can be sequentially reacted. Where, in the preferred embodiment of the invention, the focal unit is an amino acid unit of the formula I where the group X is —NH—, the reagent from which the focal unit is derived has the two amine groups protected by two different protecting groups which are removable under different conditions. Each amine group can consequently be protected, activated and reacted in sequential series of reaction steps. This allows two different dendrons to be synthesized.

The present invention includes also a method for synthesizing the novel compound in which a focal reagent which has two reactive groups is reacted in a first series of first dendron producing steps as follows:

1. reacting an amino acid reagent of the formula II

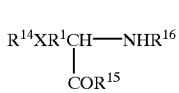

in which $R^1$ and X are as defined above, $R^{14}$ is H when X is —O—, —S— or —NH—, OH when X is —CO—, or is a protecting group, $R^{15}$ is a carboxylic acid protecting group, hydroxyl, or a carboxylic acid activating group, $R^{16}$ is H; an amine protecting group or an amine activating group, provided that at least two of $R^{14}$, $R^{15}$ and $R^{16}$ is other than an activating group and at least one of $R^{14}$, $R^{15}$ and $R^{16}$ is other than a protecting group, with a focal reagent having at least two reactive groups, optionally after a step in which the desired reactive group of the focal reagent and/or one of the groups —$XR^{14}$, —$COR^{15}$ and —$NHR^{16}$ is deprotected and/or activated whereby the reactive groups on the focal reagent reacts with one of the groups $R^{14}X$—, $R^{15}$—CO— and $R^{16}$—NH—;

2. a second step in which both unreacted groups $R^{14}X$, $R^{15}CO$— and $R^{16}NH$— of the product of the preceding step are, if necessary, deprotected and/or activated and reacted with at least two equivalents of a trifunctional reagent having the general formula II,

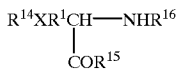

in which the groups $R^1$, $R^{14}$, $R^{15}$ and $R^{16}$ are as defined in step 1 and are the same or different as in the trifunctional reagent used in step 1;

3. (n–1) repeats of step 2, using in each case at least $2^{(q+1)}$ equivalents of trifunctional reagent for the $q^{th}$ repeat of step 2, until n levels of dendritically linked amino acids have been formed; and 4. an anchor group attachment step in which at least two of the $2^n$ groups $R^{14}X$—, $R^{15}CO$— and $R^{16}NH$ are, if necessary, deprotected and/or activated, and reacted with a lipophilic reagent of the formula III

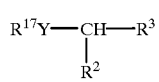

in which Y, $R^2$ and $R^3$ are as defined above, and $R^{17}$ is OH or a carboxylic acid activating group where Y is —CO—, or $R^{17}$ is H or an amine, hydroxyl or thiol activating group, respectively, where Y is —NH—, —O— or —S—, whereby the said at least two groups react with $R^{17}Y$— to conjugate

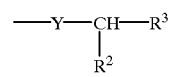

groups to the X, CO— or NH—; and a second dendron forming series of reaction steps in which 5. the other of the reactive groups of the focal reagent is, preferably in a step separate to step 1 mentioned above, reacted with an amino acid reagent of the formula II

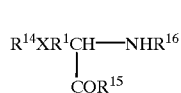

in which $R^1$ and X are as defined above, $R^{14}$ is H when X is —O—, —S— or —NH—, OH when X is —CO—, or is a protecting group, $R^{15}$ is a carboxylic acid protecting group, hydroxyl, or a carboxylic acid activating group, $R^{16}$ is H, an amine protecting group or an amine activating group, provided that at least two of $R^{14}$, $R^{15}$ and $R^{16}$ is other than an activating group and at least one of $R^{14}$, $R^{15}$ and $R^{16}$ is other than a protecting group, optionally after a step in which the desired reactive group of the focal reagent is deprotected and/or activated whereby the other or the reactive groups on the focal reagent reacts with one of the groups $R^{14}X$—, $R^{15}$—CO— and $R^{16}$—NH—;

6. in a second step, both unreacted groups $R^{14}X$—, $R^{15}CO$— and $R^{16}NH$— of the product of the preceding step are, if necessary, deprotected and/or activated and reacted with at least two equivalents of a trifunctional reagent having the general formula II,

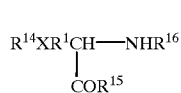

in which the groups $R^1$, $R^{14}$, $R^{15}$ and $R^{16}$ are as defined in step 1 and are the same or different as in the trifunctional reagent used in step 5;

7. (m–1) repeats of step 6, using in each case at least $2^{(p+1)}$ equivalents of trifunctional reagent for the $p^{1,h}$ repeat of step 6, until m levels of dendritically linked amino acids have been formed.

In a preferred reaction there is a preliminary step of reacting a focal reagent of the formula VI

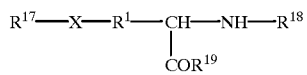

VI in which $R^{17}$, $R^{18}$ and $R^{19}$ are selected from the same groups as $R^{14}$, $R^{16}$ and $R^{15}$, respectively, as defined above, with a substrate having a pendant group which is capable of reacting with one of the groups $XR^{17}$, —$NHR^{10}$ and —$COR^{19}$, optionally after deprotection and/or activation of the said pendant group or said one of the groups of the focal reagent, whereby the focal reagent is bound to the substrate.

In the process, the series of reactions used to form the dendron having lipophilic moieties $R^2$ may be carried out before or after the series of reactions to form the other dendron. Where both dendrons are the same the series of 1–4 may be carried out simultaneously with the series of steps 5–7. Thus the reference to the first series of steps and second series of steps does not, unless the context makes it explicit, imply an order of carrying out the said series.

In the invention, in the lipophilic component —Y—CH$(R^2)R^3$, $R^2$ is preferably selected from $C_{6-24}$-alkyl, -alkenyl or -alkynyl, or is a group IV

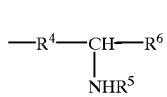

IV in which $R^4$ is a bond or a $C_{1-16}$-alkylene group, $R^5$ is hydrogen, a $C_{1-6}$-alkyl or a $C_{1-24}$-alkanoyl group or a group $CH_2SCH_2CH(OCOR^{20})CH_2OCOR^{20}$, in which $R^{20}$ is a $C_{6-24}$-alkyl, -alkenyl or -alkynyl group, $R^6$ is hydrogen or a $C_{6-24}$-alkyl, -alkoxy, -alkanoyl or -alkanoyloxy group or $R^2$ is a group of general formula IV

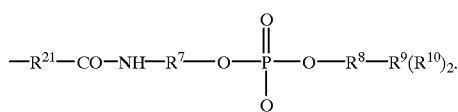

IV in which $R^8$, $R^{21}$ and $R^7$ are each $C_{2-6}$-alkylene $R^9$ glyceryl and each group $R^{10}$ is independently selected from $C_{6-24}$-alkyl, -alkenyl, -alkynyl, -alkanoyl, -alkenoyl or -alkynoyl, provided that $R^5$ and $R^6$ cannot both be groups selected from hydrogen, lower alkyl, alkenyl and alkynyl groups. Alternatively $R^2$ may be a group containing an active liquid or a sugar molecule.

Where the group $R^2$ is a group of the formula IV, and especially where $R^4$ is a bond, the compound is derived from a lipidic amino acid of the formula V

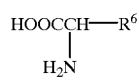

V where $R^6$ is as defined above.

In the step in which a lipidic amino acid is conjugated to the terminal branches of the first dendron whichever of the COOH and $NH_2$ group is not desired to react with the terminal branch is generally blocked by an appropriate protecting group.

It may often be more convenient to use, instead of the lipidic amino acid of the formula Vi, a monofunctional reagent to provide the anchor moieties, for instance a fatty acid or fatty amine.

The dendritic compound of the invention may be bound to a solid support, for instance a resin used as the solid peptide synthesis support. Thus the core is joined to the solid support, for instance a resin, through the focal unit, optionally via a spacer, for instance an oligopeptide spacer. The compound may be cleaved from the support prior to use, optionally after having reacted further any of the underivatised terminal branches. Thus the unreacted terminal branches may be in the form of free or protected carboxylic acid, amine, hydroxyl or thiol groups.

In a preferred aspect of the invention the dendritic compound has several terminal primary amino groups or is in the form of the corresponding ammonium salt. Usually all the terminal groups of the second dendron are amine or ammonium groups.

In a further preferred embodiment of the product of the invention, at least some of the terminal groups of the second dendron are attached to an organic group comprising a sugar molecule.

In the dendritic compound, the number of levels n and m of dendritic linked amino acid units in the two dendrons may be the same or is, usually, different. Generally it is preferred for all of the terminal branches of the first dendron to be provided with lipophilic anchor moieties. It is found that two or four such moieties are adequate to provide appropriate levels of lipophilicity to the compound as a whole. Consequently it is preferred for the first dendron to have two levels of dendritically linked amino acid units (that is n is 2).

The second dendron generally has at least three levels of dendritically linked amino acid units, preferably four or, sometimes five levels of dendritically linked amino acid units (that is m is 3 to 5). Where there are five or more levels of dendritically linked amino acid units, stearic hindrance may prevent full dendritic linkage of groups, for instance further dendritic moieties, to the terminal units. Consequently it is preferred for there to be no more than five, and preferably four, levels of dendritically linked amino acid units.

As indicated below in the detailed examples, it has been found that the dendrimer of the present invention having four anchor groups being lipidic amino acid units joined to the amine terminal groups of the first dendron, and with free amino groups at each of the terminal groups of 3-, 4- and 5-level dendritically linked amino acid units for the second dendron have reduced toxicity as determined by erythrocyte lysis, as compared to a lipid peptide dendromer as described in our earlier application WO-A-94/02506 comprising a linear oligopeptide anchor moiety of three lipidic amino acids joined to the focal lysine of a dendrimer having the equivalent number of levels of dendritically linked amino acid (lysine) units.

The compound of the invention has a similar utility to those described in WO-A-94/02506. Thus, to the terminal branches of the one or other or both, preferably second dendron, there may be conjugated peptide antigens, drug moieties, targeting moieties, for instance antibodies or sugar groups, or other groups providing increased levels of hydrophilicity (for instance sugar molecules, polyethylene glycol molecules or ionic moieties).

The invention is illustrated further in the following examples.

MATERIALS AND METHODS

Polystyrene aminomethylated (PAM) resin, BOC-protected aminoacids from Novabiochem, 2-(1H benzotriazole-lyl)-1,3,3-tetramethyluronium hexafluorophosphate (HBTU) from Phase Separations Ltd, Trifluoroacetic acid (RFA) from Halocarbon Products Corporation, hydrogen fluoride gas (HF) from BOC, diisopropyl ethyl amine (DIEA) from Fluka and dimethylformaamide (DMF) from Rathburn were all used as received. The protected lipidic aminoacids were synthesized and purified in our laboratory as described in Gibbons, Wash., et al (1990) liebigs Ann. Chem. 1177–1183.

EXAMPLE 1

Solid phase peptide synthetic methods were used employing a polyacrylamide resin having a degree of substitution of 0.46 mmol/g resin. The reaction sequence is shown in slow diagram FIG. 1 the step involving protection of Boc was performed in 100% trifluoroacetic acid. Couplings of pendant amine groups on the bound compound with carboxylic acid groups of amino acid reagents having protected amine groups was achieved using a three fold excess of HBTU activated Doc-amino acids in dimethylformamide in the presence of diisopropylethyl amine. Acidulation of deprotected Boc group of lipoamino acid was carried out in the presence of diisopropylethyl amine. Deprotection of the Fmoc group to form the second dendron was carried out by a suitable system.

The resin peptide was carefully flow washed before and after each deprotection step. The final product was washed with dichloromethane and dried in air. The peptide was removed from the resin support with a high HF method 2 g resin peptide, 20 ml HF, 1.5 hour at −5° C.) to yield the crude peptide which was dissolved in 95% acetic acid solution and lyophilised.

Purification

Analytical HPLC separation of the synthesized dendrimers was carried out on a 25 cm Vydac $C_{18}$ RAC column with 5 μm pore size and 4.6 mm internal diameter. Following standard degassing techniques, particulate matter was removed from HPLC grade acetonitrile and water using membrane filters. Analytical separation was achieved with a solvent gradient beginning with 0% acetonitrile, increasing to 60% acetonitrile at 20 min. maintaining at this concentration for 20 min and decreasing steadily to 0% acetonitrile for 10 min at a constant flow of 1.2 ml min$^{-1}$. For preparative separation a TSK-GEL preparative $C_{18}$ column with 10 μm pore size and 2.5 cm internal diameter was used. Separation was achieved with a solvent gradient beginning with 0% acetonitrile, increasing constantly to 18% acetonitrile at 60 min then 60% acetonitrile at 80 min, staying at this concentration for further 30 min and decreasing steadily to 0% acetonitrile for 30 min at a constant flow of 8 ml min$^{-1}$. The gradient was effected by two microprocessor-controlled Gilson 302 single piston pumps. Compounds were detected with a Waters 486 tunable absorbance detector at 214 nm or a Holocrome UV-VIS detector 220 nm. Mass spectra were fun on VG Analytical Tofspec instrument, using matrix assisted laser desorption (MALD) ionisation at a wavelength of 337 nm generated by a nitrogen laser.

Compound synthesis using the general technique mentioned above had the following general structure:

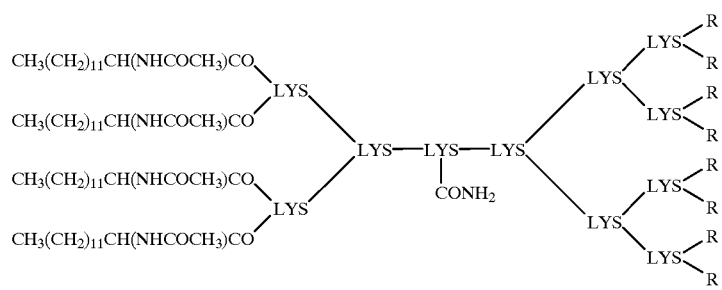

The compounds synthesised have the values for the number of lipid residues and the number of primary amine groups as well as the molecular weight shown in Table 1.

TABLE 1

| Compound | R | Levels of dendritically linked lys residues in 2nd dendron | No of primary amine groups | MW |
| --- | --- | --- | --- | --- |
| 1.1 | NH$_2$ | 3 | 8 | 2500 |
| 1.2 | Lys(NH$_2$)$_2$ | 4 | 16 | 3526 |
| 1.3 | Lys(Lys(NH$_2$)$_2$)$_2$ | 5 | 32 | 5577 |

COMPARATIVE EXAMPLE 1

Using the same general techniques described above in relation to Example 1, but omitting the Fmoc strategy, compounds having the general formula shown below were produced. Thus the process involved three sequential steps to provide a linear tripeptide of lipoamino acid units bound to the glycine group attached to the resin, followed by a step of adding a Boc Lys (Boc) OH unit to the third lipoamino acid unit, followed by deprotection of both the amine groups of lysine and addition of sequential dendritically linked lysine moieties.

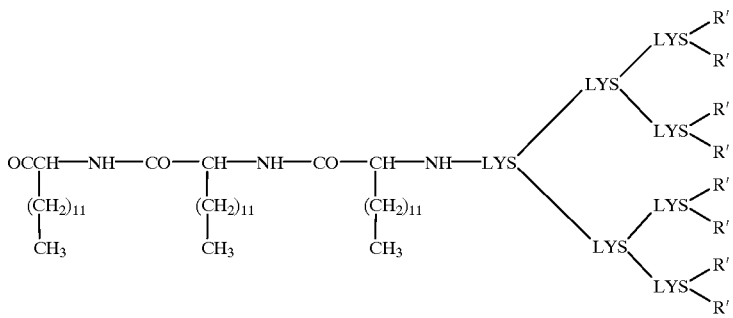

The methylol compound was synthesized by subjecting the compound having eight free amine groups at the terminal ends to reaction with a suitable reagent. The compounds synthesized are shown in Table 2 below.

TABLE 2

| Compound | R' | Levels of dendritically linked Lys (n) | No of primary amine groups | MW |
|---|---|---|---|---|
| 1.4 | $NH_2$ | 3 | 8 | 1590 |
| 1.5 | $Lys(NH_2)_2$ | 4 | 16 | 2615 |
| 1.6 | $Lys(Lys(NH_2)_2)_2$ | 5 | 32 | 4666 |
| 1.7 | $CH_2OH$ | 3 | 0 | 3390 |

Rat Erythrocyte Lysis Studies

Fresh blood was obtained from rats through cardiac puncture, collected in haparinised tubes and centrifuged at 1,000 g for 15 minutes at 4° C. The supernatant, was discarded, the volume was made up to 10 ml with chilled phsophate buffered saline (PBS). The suspension was centrifuged again and the PBS washing step was repeated twice. Finally, the supernatant was removed and the cell pellet resuspended up to 2% w/v in chilled PBS. 100 µl or samples of compounds 1.1–1.7 of different dilutions were added in flat bottomed Elisa plate. 1% w/v of Triton X 100 was used as the control (100% lysis). 100 µl of erythrocyte suspension was added and incubated for 1h, 5 h and 24 hrs. At different time intervals these plates were removed and the suspensions centrifuged. 100 µl of the supernatant was removed and placed into fresh Elisa plate and the absorbance was measured at 545 nm with PBS as blank. The % population lysis was calculated by using the formula Percentage population lysis=(Absorbance/control (triton) absorbance) 100.

Results

The toxicity of compounds 1.1–1.7 were compared with linear polylysine of two different molecular weights (34,000 and 1000–4000). Triton X100 was used as positive control. The higher M.W. polylysine had a concentration independent toxicity 35.7% to 54.2% of percent population lysis was observed between the concentrations 1 µg/ml to 30 µg/ml. The lower M.W. polylysine was found to be almost non-toxic.

Red blood cellsysis studies indicatee that compounds 1.4 1.6 were non toxic at the low concentration of 1 µg/ml after 24 hrs where as at higher concentrations (about 20 µg/ml) these compounds were toxic even after one hour incubation. All compounds 1.1–1.6 had concentration dependent toxicity.

The toxicity studies of compounds 1.1 to 1.3 showed that the toxicity is dependent on the ratio of the lipophilic groups to the number of amino groups attached to the molecule. Compound 1.1, which contained 8 amino groups found to be less toxic than similar compounds having 16 and 32 amino groups (1.2 and 1.3) were less toxic than comparative 1.4 to 1.6. This indicates that although compounds 1.1 to 1.3 were bulkier, the position of attachments of lipo amino acid makes them less toxic.

Compound 1.7 which contained 3 lipo amino acid chain attached consecutively was non toxic at the concentration of 30 µg/ml up to 5 hours incubation, indicating that the toxicity is not due to the presence of lipo amino acid.

Figure 2:
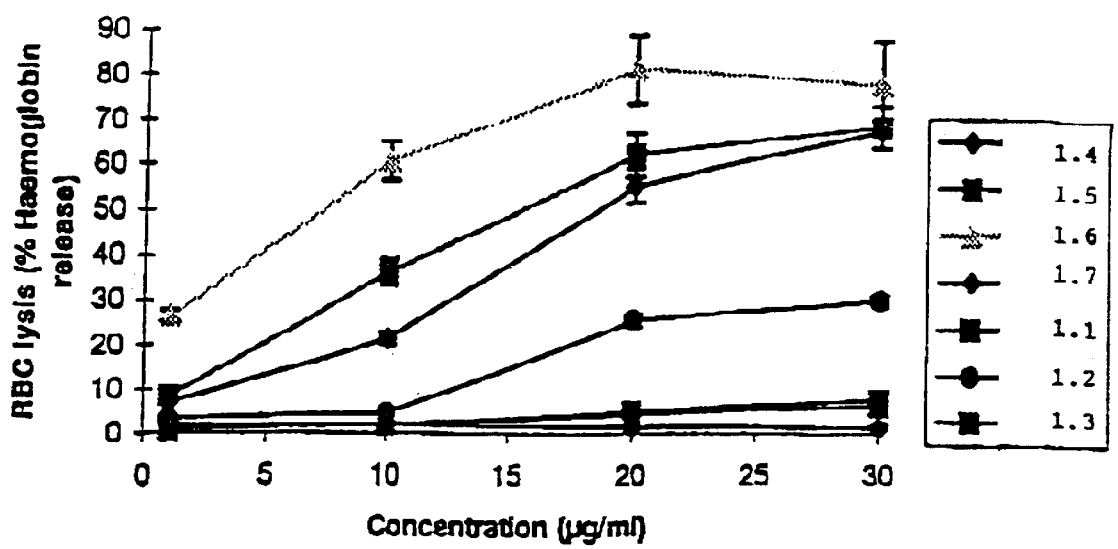
FIG. 2 is a graph of hemoglobin release.
Figure 3:
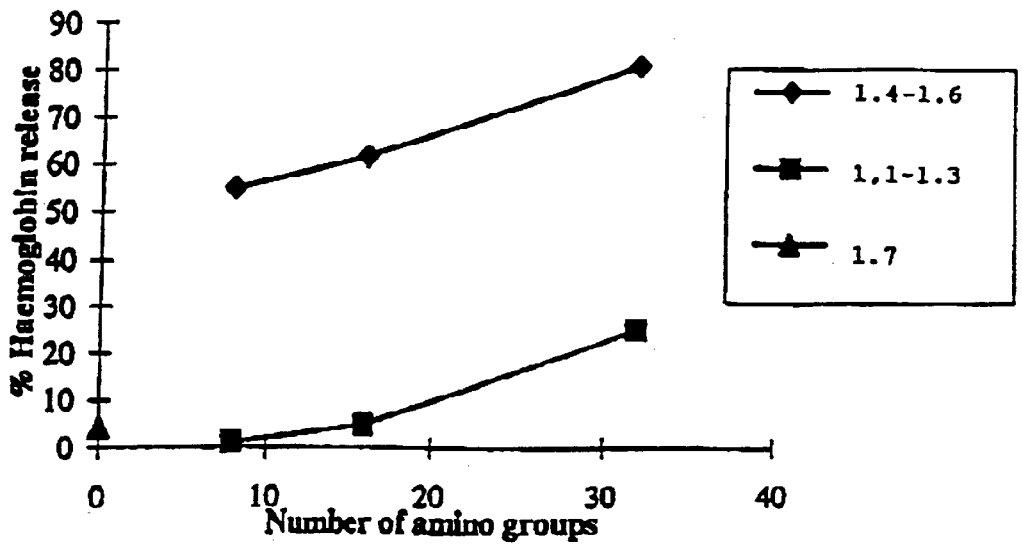
FIG. 3 is a graph of the relationship between the number of amino groups and hemoglobin release.

The results are illustrated graphically in FIGS. 2 and 3.

EXAMPLE 2

A compound having two identical dendrons, each comprising 3 levels of dendritically linked lysine units and a lysine focal unit, and having each terminal amino group linked to a lipidic amino acid anchor group $CH_3(CH_2)_{11}CH(NHCOCH_3)CO-$ having a tritiated acetyl moiety was synthesized using the same technique as Example 1. The diameter of a particle constituted by the molecule is calculated as 2.5 nm.

Stability

The stability of the tritiated dendrimer was examined in biological fluids such as plasma, serum and gastrointestinal scrapings (dendrimer-biological fluids ratio 1:2, 1:5 and 1:20) using a dialysis bag with molecular weight cut off 5000 daltons and PRS as dialysis medium and its biodistribution after oral, intraperitoneal and administration in female Sprague-Dawley rats (dose: 14 mg/kg; 0.2 ml).

The degradation of the dendrimer in biological fluids such as GI scrapings, rat plasma and foetal calf serum was performed. Degradation resulted in the formation of fragments, detected in the dialysis medium. No degradation was observed in 1:2 and 1:5 dendrimer biological fluid ratios whereas the 1:20 ratio caused 7–22% breakdown of dendrimer after 24h incubation.

Oral biodistribution study

The amount of radiolabel recovered after different time intervals after oral administration of 14 mg/dosage in gastrointestinal tract and other organs such as liver, spleen, kidneys and blood were measured. In small intestine, 15% of the dose administered was recovered after 6 hrs.

A maximum of 1.2% was recovered in the liver after 6h but less than 1% was found in spleen and kidney. In blood 3% of the administered radiolabel was found after 6h. After oral administration the bioavailability of the dendrimer was found to be 17.3% after 3h 26.4% after 6h and 1.2% after 24h.

The results show preferential uptake (per gram tissue) of the dendrimer through lymphoid tissue in the small intestine but not in the large intestine after oral administration in female Sprague-Dawley rats are as follows. The uptake through lymphoid tissue of the small intestine was 1.09% after 3h and gradually decreased after 6h (0.23%) and 12 h (0.05%). The uptake through the non-lymphoid small intestine was 3.8%, 2.5% and 0.3% after 3.6 and 12 h respectively. The uptake through lymphoid tissue of the large intestine was negligible whereas uptake through the non-lymphoid large intestine gradually increased from 1.06% at 3h to 3.8% at 12 h.

After 24h, less than 1% of the administered dose was recovered.

Intraperitoneal distribution study

The radioactivity observed in liver after 3 h and 24 h were 2.4% and 10% respectively for a dosage i.p. of 14 mg/kg.

Conclusion

The results clearly indicate that the dendrimer is quite stable in biological environment and its biodistribution studies indicate that it behaves similar to other colloidal carriers. Dendrimers have potential to be used as carriers for the delivery of bioactive molecules.

What is claimed is:

1. A dendritic compound consisting of a focal group from which a first dendron and a second dendron extend, the first dendron comprising dendritically linked amino acid units I

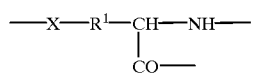

in which $R^1$ is $C_{1-6}$-alkylene and X is selected from the group consisting of —O—, —S—, —NH— and —CO—, and each unit of the first dendron has individually selected groups $R^1$ and X, and wherein the first dendron has n levels (where n is at least 1) of said dendritically linked amino acid units and $2^n$ terminal branches, and wherein at least 2 of which terminal branches are directly linked to anchor groups

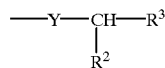

where Y is selected from —CO—, —NH—, —O— and —S—, provided that at least one of X and Y is —CO—, $R^2$ is a $C_{6-24}$-alkyl, -alkenyl, or -alkynyl group, $R^3$ is selected from the group consisting of hydrogen, amine, blocked amine, hydroxyl, $C_{1-24}$ alkoxy, thio, COOH, and organic groups containing at least one $C_{6-24}$-alkyl, -alkenyl or -alkynyl group, $C_{1-6}$-alkanoyloxy, or $C_{1-6}$-alkanoylamino groups, any of which may be substituted by a sugar moiety, and in which the second dendron has m levels (where m is 2 or more) of dendritically linked amino acid units of the formula I above in which the groups $R^1$ and X may be the same as or different from one another and the same as or different from those of the amino acid units in the first dendron and wherein the second dendron has $2^m$ terminal branches, each of which is selected from the group consisting of $NH_2$, $N^+H_2R^{11}$, in which $R^{11}$ is hydrogen or $C_{1-4}$-alkyl, COOH, COO$^-$, OH, SH, —$XR^{12}$, —$NHR^{12}$ or —$COR^{12}$ where $R^{12}$ is a hydroxymethyl group.

2. A compound according to claim 2 in which the focal group is an amino acid unit having the formula I

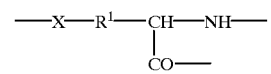

in which the first dendron is joined to one of the bonds, the second dendron is attached to one of the remaining two bonds and the third bond is attached to an organic group.

3. A compound according to claim 1 in which X in the focal group is —CO— or —NH—.

4. A compound according to claim 3 in which the focal unit is formed from lysine or ornithine, that is $R^1$ is $(CH_2)_4$— or —$(CH_2)_3$ and X is in each case is —NH—.

5. A compound according to claim 3 in which in each of the groups of the formula I, the groups $R^1$ and X are the same.

6. A compound according to claim 1 in which $2^n$=p.

7. A compound according to claim 1 in which n is 2.

8. A compound according to claim 1 in which m is 3 to 5.

9. A compound according to claim 1 in which each terminal branch of the second dendron is —$NH_2$ or —$N^+H_2R^{11}$, where $R^{11}$ is hydrogen or —$C_{1-4}$alkyl.

10. A compound according to claim 1 in which in each of the groups of the formula I, the groups $R^1$ and X are the same.

11. A compound according to claim 10 in which X is —NH— and $R^1$ is —$(CH_2)_4$— or —$(CH_2)_3$—.

12. A compound according to claim 1 which is bound to a resin support through the focal group.

13. The compound according to claim 1 wherein the second dendron, $R^1$ is the same at every occurrence, and X is the same at every occurrence.

14. The compound according to claim 1, wherein the second dendron, all $R^1$ substituents are identical to one another, and concomitantly all X substituents are identical to one another.

15. A composition comprising a compound of claim 1.

16. A pharmaceutical composition comprising a pharmaceutical excipient and a compound according to claim 1.

17. A dendritic compound comprising a focal group from which a first dendron and a second dendron extend, the first dendron consisting of 2 levels of dendritically linked amino acid units I

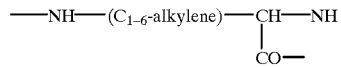

in which each unit may have the same or different alkylene group, whereby there are 4 terminal branches, to each of which terminal branches there are linked anchor groups

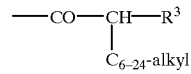

where $R^3$ is hydrogen or $C_{1-6}$-alkanoylamino, and in which the second dendron has m levels (where m is 3 to 5) of dendritically linked amino acid units of said formula I in which the units may be the same as or different from one another and the same as or different from those of the amino acid units in the first dendron and $2^m$ terminal branches, each of which is selected from the group consisting of $NH_2$, $N^+H_2R^{11}$, in which $R^{11}$ is hydrogen or $C_{1-4}$ alkyl, and —$NHR^{12}$ where $R^{12}$ is a peptide antigen or Boc.

18. A method of synthesizing a compound according to claim 2 in which a focal reagent which has two reactive groups is reacted in a first series of first dendron producing steps as follows:

(a) reacting an amino acid reagent of the formula II

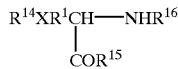

II in which $R^1$ and X are as defined in claim 1

$R^{14}$ is H when X is —O—, —S— or —NH—, OH when X is —CO—, or is a protecting group, $R^{15}$ is a carboxylic acid protecting group, hydroxyl, or a carboxylic acid activating group, $R^{16}$ is H, an amine protecting group or an amine activating group, provided that at least two of $R^{14}$, $R^{15}$ and $R^{16}$ is other than an activating group and at least one of $R^{14}$, $R^{15}$ and $R^{16}$ is other than a protecting group, with a focal reagent having two reactive groups, optionally after a step in which the desired reactive group of the focal reagent is deprotected or activated or both whereby at least one of the reactive group on the focal reagent reacts with one of the groups $R^{14}$X—, $R^{15}$—CO— and $R^{16}$—NH—;

(b) a second step in which both unreacted groups $R^{14}$X—, $R^{15}$CO— and $R^{16}$NH— of the product of the preceding step are, if necessary, deprotected or activated or both and reacted with at least two equivalents of a trifunctional reagent having the general formula II,

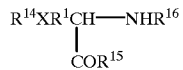

II in which the groups $R^1$, $R^{14}$, $R^{15}$ and $R^{16}$ are as defined in step (a) and are the same or different as in the trifunctional reagent used in step (a);

(c) (n−1) repeats of step (b), using in each case at least $2^{(q+1)}$ equivalents of trifunctional reagent for the $q^{th}$ repeat of step (b), until n levels of dendritically linked amino acids have been formed; and (d) an anchor group attachment step in which at least two of the $2^n$ groups $R^{14}$X—, $R^{15}$CO— and $R^{16}$NH— are, if necessary, deprotected or activated or both, and reacted with a lipophilic reagent of the formula III

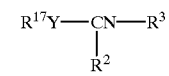

III in which Y, $R^2$ and $R^3$ are as defined above, and $R^{17}$ is OH or a carboxylic acid activating group, where Y is —CO— or is H or an amine, hydroxyl or thio activating group, respectively, where Y is —NH—, —O— or —S—, whereby the said at least two groups react with $R^{17}$Y— to conjugate

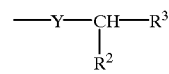

groups to the X, CO— or NH—; and a second dendron forming series of reaction steps in which (e) the other of the reactive groups of the focal reagent is, in the same step or in a step separate to step (a) of the first series of first dendron producing steps, reacted with an amino acid reagent of the formula II

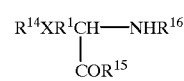

II in which $R^1$ and X are as defined above, $R^{14}$ is H when X is —O—, —S— or —NH—, OH when X is —CO—, or is a protecting group, $R^{15}$ is a carboxylic acid protecting group, hydroxyl, or a carboxylic acid activating group, $R^{16}$ is H, an amine protecting group or an amine activating group, provided that at least two of $R^{14}$, $R^{15}$ and $R^{16}$ is other than an activating group and at least one of $R^{14}$, $R^{15}$ and $R^{16}$ is other than a protecting group, optionally after a step in which the desired reactive group of the focal reagent or one of the groups —$XR^{14}$, —$COR^{15}$ and —$NHR^{16}$ or both is deprotected or activated or both whereby the other of the reactive groups on the focal reagent reacts with one of the groups $R^{14}$X—, $R^{15}$—CO— and $R^{16}$—NH—;

(f) a second step in which both unreacted groups $R^{14}$X—, $R^{15}$CO— and $R^{16}$NH— of the product of the preceding step are, if necessary, deprotected or activated or both and reacted with at least two equivalents of a trifunctional reagent having the general formula II,

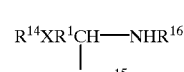

II in which the groups $R^1$, $R^{14}$, $R^{15}$ and $R^{16}$ are as defined in step (a) and are the same or different as in the trifunctional reagent used in step (a):

(g) (m−1) repeats of step (f), using in each case at least $2^{(p+1)}$ equivalents of trifunctional reagent for the $p^{th}$ repeat of step (b), until m levels of dendritically linked amino acids have been formed.

19. A method according to claim 18 involving a preliminary step of reacting a focal reagent of the formula VI

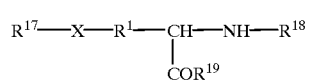

VI in which $R^{17}$, $R^{18}$ and $R^{19}$ are selected from the same groups as $R^{14}$, $R^{16}$ and $R^{15}$, respectively, with a substrate having a pendant group which is capable of reacting with one of the groups —$XR^{17}$, —$NHR^{18}$ and —$COR^{19}$, optionally after deprotection or activation or both of the said pendant group, whereby the focal reagent is bound to the substrate.

20. A method according to claim 19 in which the substrate is an immobile support.

21. A method according to claim 20 in which the resin has pendant amine groups and in which the group —$COR^{19}$ is reacted with said pendant amine groups in the presence of an activating compound to form a peptide bond.

22. A method according to claim 21 in which $R^{17}$ and $R^{18}$ are each different amine protecting groups.

23. A method according to claim 19 in which the immobile support is a polyacrylamide-based resin.

24. A method according to claim 18 in which in each of the steps in each respective series the reagent of the formula II is the same.

25. A method according to claim 24 in which X is —NH— and in which the groups $R^{14}$ and $R^{15}$ are the same amino protecting groups.

* * * * *